United States Patent [19]

Meyer et al.

[11] 4,267,362

[45] May 12, 1981

[54] PROCESS FOR THE PREPARATION OF DELTA KETO-ACIDS AND DERIVATIVES THEREOF

[75] Inventors: Peter J. N. Meyer, Munstergeleen; Josef M. Penders, Maastricht, both of Netherlands

[73] Assignee: Stamicarbon, B.V., Geleen, Netherlands

[21] Appl. No.: 67,914

[22] Filed: Aug. 17, 1979

[30] Foreign Application Priority Data

Aug. 19, 1978 [NL] Netherlands ......................... 7808605

[51] Int. Cl.³ ................ C07C 120/00; C07C 121/34; C07C 121/46; C07C 64/716
[52] U.S. Cl. ..................................... 560/174; 260/464; 260/465.1; 560/126; 562/577; 562/508
[58] Field of Search ................ 260/464, 465.1, 561 K, 260/557 R; 560/174, 126; 562/577, 508

[56] References Cited

U.S. PATENT DOCUMENTS

| | | | |
|---|---|---|---|
| 2,381,371 | 8/1945 | Shannon | 260/465.1 |
| 2,386,736 | 4/1941 | Bruson | 562/577 X |
| 2,579,580 | 12/1951 | Howk et al. | 260/465.1 |
| 2,773,087 | 12/1956 | Stork | 560/126 X |
| 2,850,519 | 9/1958 | Krimm | 562/577 X |
| 3,150,142 | 9/1964 | Eby | 260/561 K |
| 3,759,973 | 9/1973 | Cherubim et al. | 562/508 X |
| 3,780,083 | 12/1973 | Deumens et al. | 260/465.1 |
| 3,816,503 | 6/1974 | van Poelvoorde et al. | 260/465.1 X |
| 3,931,278 | 1/1976 | Muller | 260/465.1 |
| 4,117,000 | 9/1978 | Balg et al. | 260/465.1 |

*Primary Examiner*—Joseph P. Brust
*Attorney, Agent, or Firm*—Cushman, Darby & Cushman

[57] ABSTRACT

A process is described for the preparation of delta keto-acids wherein there is used as a catalyst the condensation adduct of a cyclic secondary amine with an α-β-acrylic-type unsaturated compound, providing high selectivity and conversion results.

14 Claims, No Drawings

PROCESS FOR THE PREPARATION OF DELTA KETO-ACIDS AND DERIVATIVES THEREOF

This invention relates to a process for the preparation of delta keto-acids and derivatives thereof by reaction in the liquid phase of a ketone with an acrylic acid or an acrylic-acid derivative.

A reaction of this type, which is generally known by the name of Michael's addition, can give products that are suitable as starting materials for the preparation of other valuable end-products. For instance, the delta keto-acid ester obtained upon addition of an acrylic ester to cyclohexanone can be converted into dihydrocoumarin, which is important in the perfume industry (see U.S. Pat. No. 3,442,910). The addition of acrylic acid or an acrylic ester to acetone yields a compound that can be converted by cyclization into dihydroresorcinol, which can be dehydrogenated to form resorcinol, a well-known starting material in the plastics industry.

It is now commonly known (see, for instance, British Patent Specifications Nos. 1,303,949, 1,389,510 and 1,476,153) to use a primary amine or a Schiff base as a catalyst in the addition of a ketone, having at least one activated alpha H-atom, to an acrylic acid or the ester or the nitrile of such acid. Also, a secondary amine, such as piperidine, has been mentioned as a catalyst for such a reaction (see Adams, Organic Reactions, vol. 10, p. 415–477, John Wiley and Sons 1959).

In the present invention, a catalyst has now been found which provides better results in said addition reaction.

In the process according to the present invention, the preparation of delta keto-acids and derivatives thereof by reaction in the liquid phase of a ketone having at least one activated alpha H-atom with an acrylic acid or an acrylic-acid derivative and with the aid of a catalyst is carried out using as the catalyst the condensation adduct of a cyclic secondary amine with an α-β-acrylic-type unsaturated compound (added to the amine group).

When a catalyst according to this invention is used, a higher selectivity, both with respect to the ketone and with respect to the acrylic compound, and a lower catalyst consumption can be achieved than is observed with the use of the known catalysts.

The process according to the invention may use various ketone-starting materials, such as, e.g., acetone, methyl-ethyl ketone, methyl-propyl ketone, diethyl ketone, methyl-isopropyl ketone, cyclopentanone, cyclohexanone, 2-methyl cyclohexanone, and 4-methyl cyclohexanone, i.e., aliphatic and cyclo-aliphatic ketones having up to about 10 carbon atoms. The process according to the invention is particularly suitable for the conversion of acetone and cyclohexanone.

Various acrylic acids and derivatives thereof may be used in the process according to the invention. Of practical importance are, especially, acrylic acid, methacrylic acid, crotonic acid, and also the lower alkyl esters, the nitriles and the amides of these acids. Very good results can be obtained with the use of the methyl ester and ethyl ester or of the nitrile of said acids.

The ratio between the amount of ketone and the amount of acrylic compound may be varied. Theoretically, 1 mole of ketone is required per mole of acrylic compound. In most cases, excess ketone of up to a 10:1 mol ratio is used in the conversion of the alkyl ketone. An amount of over 10 moles of alkyl ketone per mole of acrylic compound may be used, but does not lead to any practical advantage. The best ratio of ketone to acrylic compound can readily be determined experimentally in practice.

The catalyst according to this invention is based on various cyclic lower alkyl secondary amines, such as, e.g., pyrrolidine, piperidine, morpholine and piperazine (i.e., cyclic amines of from 4 to 7 ring atoms of N, C or O), which amines may carry a substituent lower alkyl group of from 1 to 4 carbon atoms at one or more of the ring carbon atoms. The ring-lower-alkyl groups may contain up to about 6 carbon atoms. Of such amines, pyrrolidine is very suitable, because not only a high selectivity, but also a satisfactory conversion can be achieved therewith.

The α-β-unsaturated compound on which the catalyst is also based may be chosen differently. Very suitable are acrylic acid, methacrylic acid, crotonic acid, lower alkyl esters of these acids, such as the methyl and ethyl esters, and the amides or nitriles of said acids. That is, there are used the α,β-unsaturated lower aliphatic compounds of the general formula

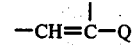

wherein Q represents a carboxylic acid or carboxylic lower alkyl ester or carboxamide or a nitrile group. In practice, the acrylic compound preferably used as the α-β-unsaturated compound for the catalyst is the same as that entering into reaction with the ketone.

The addition of the α-β-unsaturated compound to the cyclic secondary amine (via the —N—H group) may be effected in a known way, e.g., in the way described in Bull. Soc. Chim. France, 1971 No. 5, p. 1717 ff. and J. Am. Chem. Soc., vol. 66, 1944 pp. 725–731.

The amount of catalyst used may be varied. Amounts of between about 0.05 to 0.5 mole of catalyst per mole of acrylic compound to be converted are very satisfactory in practice.

If a minor amount of a weak or strong acid compound is also present, in addition to the catalyst, it may result in an improvement of the selectivity. Examples of such suitable additional acid compounds are organic carboxylic acids such as acetic acid, adipic acid, benzoic acid, phenol, caproic acid; mineral acids such as hydrochloric acid, phosphoric acid, sulphuric acid; and weak base salts of strong acids such as ammonium chloride. For instance, 0.001–0.1 mole of such acid compound may be used per mole of catalyst.

The process according to the invention is usually carried out at a temperature of between about 130° and 250° C. At temperatures above about 250° C., the selectivity of the reaction is decreased, while at temperatures below about 130° C., the reaction proceeds too slowly. Temperatures of between about 170° and 230° C. are particularly suitable.

The pressure is not critical and may be widely varied, except that the pressure must, of course, be so chosen that the reaction takes place in the liquid phase, whether or not in the presence of a solvent or diluent vehicle.

The ketone and/or the acrylic compound may be fully or partly converted in the process according to the invention. Preferably, about 20 to 90% of the acrylic component is converted. Working at conversions of over 90% may have an adverse effect on the selectivity of the reaction, while at conversions of below 20% there is too large a recirculation requirement for the unconverted starting product. After the desired conversion level has been reached, the reaction products can be separated by distillation, in which, besides the desired product, a fraction rich in catalyst can be separated off which may be re-used.

The invention will now be further elucidated and understood in the following examples.

EXAMPLE I 290.0 grams of acetone, 86.0 grams of methyl acrylate, 19.6 grams of methyl-$\beta$-pyrrolidin-1-yl propionate (addition product of pyrrolidine and methyl acrylate) and 0.2 grams of benzoic acid are placed together in a 1-liter autoclave. The mixture in the autoclave is heated to 170° C., under autogenous pressure, and kept at this temperature for 3 hours. The reaction mixture is then cooled and transferred to a distillation flask. The mixture is separated into 316.2 grams of distillate boiling below 132° C. and 79.6 grams of residue by distillation at atmospheric pressure. Gas-chromatographic analysis, shows that the distillate contains 263.4 grams of acetone and 49.6 grams of methylacrylate. According to gas-chromatographic analysis, the residue contains 18.9 grams of methyl-$\beta$-pyrrolidin-1-yl propionate and 58.2 grams of the methyl ester of delta-oxocaproic acid. The residue is then separated by fractional distillation into a first-running fraction of 20.8 grams with a boiling point of 112°–114° C. at 5.3 kPa, and a main fraction of 56.5 grams with a boiling point of 121.5°–122.5° C., at 5.3 kPa. According to gas-chromatographic analysis, the first-running fraction contains 89.7% of methyl-$\beta$-pyrrolidin-1-yl propionate ($n_D^{23} = 1.4514$) and the main fraction 99.8% of 4-oxopentane-carboxylic methyl ester ($n_D^{23} = 1.4270$).

42.3% of the total amount of methyl acrylate has thus been converted. The yield is 88.0% with respect to the amount of acetone consumed and 95.4% with respect to the amount of methyl acrylate converted.

In order to prepare the above catalyst adduct addition product, 0.12 mole of pyrrolidine is added, at room temperature, to a solution of 0.12 mole of methyl acrylate in 40 milliliters of ether, after which the mixture is heated with reflux cooling for 24 hours. The ether is then evaporated and the residue is distilled at 2.6 kPa.

Generally, this latter procedure is adopted for the preparation of the other catalyst adducts used herein.

COMPARATIVE EXAMPLE

Example I is repeated except that 8.9 grams of pyrrolidine are added instead of 19.6 grams of methyl-$\beta$-pyrrolidin-1-yl propionate. After three hours reaction at 170° C. under autogenous pressure, the reaction mixture contains 90.9 grams of methyl ester of the delta-oxocaproic acid and 7.3 grams of methyl acrylate according to gas-chromatographic analysis. The yield of the desired product is only 69.0% with respect to converted methyl acrylate and only 65.2% with respect to acetone.

EXAMPLE II 34.8 grams of acrylonitrile, 292.4 grams of acetone, 9.4 grams of $\beta$-pyrrolidin-1-yl propionitrile (the addition product of pyrrolidine and acrylonitrile) and 0.06 gram of acetic acid are placed together in a 1-liter autoclave. The mixture is heated at 200° C. for 4 hours under autogenous pressure. After cooling, the mixture is analyzed gas-chromatographically. According to the analysis, the reaction mixture contains 9.0 grams of acrylonitrile, 238.4 grams of acetone and 47.1 grams of delta-oxocapronitrile. This achieves an acrylonitrile conversion of 74.1%. The yield of delta-oxocapronitrile is 82.0% with respect to converted acetone and 87.4% with respect to converted acrylonitrile.

EXAMPLE III 245.0 grams of cyclohexanone, 244.6 grams of methyl acrylate, 30.4 grams of methyl-$\beta$-pyrrolidin-1-yl propionate and 0.1 grams of benzoic acid are placed together in a 1-liter autoclave. The mixture in the autoclave is heated to 170° C. under autogenous pressure and kept at this temperature for 2 hours. The reaction mixture is then cooled and analyzed gas-chromatographically. 40.4 grams of methyl acrylate are detected, while 439.0 grams of methyl-3-(2-oxocyclohexyl) propionate have formed.

The yield of methyl-3-(2-oxocyclohexyl) propionate with respect to the amount of methyl acrylate converted is essentially quantitative and is 99.2% with respect to the amount of cyclohexanone converted.

EXAMPLE IV 290.0 grams of acetone, 82.8 grams of methyl acrylate, 23.8 grams of methyl-$\beta$-piperidin-1-yl propionate (addition product of piperidine and methyl acrylate) and 0.7 grams of benzoic acid are placed together in a 1-liter autoclave. The mixture in the autoclave is heated to 210° C. under autogenous pressure and kept at this temperature for 4 hours. After cooling, the reaction mixture is analyzed gas-chromatographically. 66.6 grams of methyl acrylate are detected, while 24.2 grams of delta-oxocaproic acid have formed. The yield of delta-oxocaproic methyl ester is consequently 89.1% with respect to converted methyl acrylate and 92.0% with respect to the amount of acetone converted.

EXAMPLE V 290.0 grams of acetone, 83.5 grams of methyl acrylate, 16.8 grams of $\beta$-pyrrolidin-1-yl propionitrile (addition product of pyrrolidine and acrylonitrile) and 0.6 grams of benzoic acid are put together in a 1-liter autoclave. The mixture in the autoclave is heated to 200° C. under autogenous pressure and kept at this temperature for 2 hours. After cooling, the mixture is analyzed gas-chromatographically. 65.5 grams of methyl acrylate are detected, while 24.2 grams of delta-oxocaproic acid methyl ester have formed. Hence, the yield of delta-oxomethyl caproate is 90.1% with respect to the amount of methyl acrylate converted and 78.0% with respect to the amount of acetone converted.

It should be understood that the practice of this invention includes modifications from the specific teachings of the foregoing Examples, as will be apparent to those skilled in the art, and is limited only by the spirit and scope of the following claims.

What is claimed is:

1. In a process for the preparation of delta-keto-acids and derivatives thereof by reaction of aliphatic or cyclo-aliphatic ketones having at least one activated alpha H-atom with an acrylic compound in the liquid phase and with the aid of a catalyst, the improvement consisting essentially in the combination of
   (i) using as said ketone a member of the group consisting of acetone, methyl-ethyl ketone, diethyl ketone, methyl-propyl ketone, methyl-isopropyl ketone, cyclopentanone, cyclohexanone, 2-methyl cyclohexanone, and 4-methyl cyclohexanone;

(ii) using as said acrylic compound a member of the group consisting of acrylic acid, methacrylic acid, crotonic acid, the lower alkyl esters of these acids, the nitriles of these acids and the amides of these acids;

(iii) using as said catalyst the adduct of a cyclic secondary amine and an acrylic compound as defined in (ii) herein.

2. Process according to claim 1, wherein the cyclic secondary amine used is pyrrolidine.

3. Process according to either one of the claims 1 or 2, wherein the said acrylic compound to be converted is the same as the acrylic compound used in the catalyst adduct.

4. Process according to claim 1, wherein from 0.05 to 0.5 mole of said catalyst is used per mole of acrylic compound to be converted.

5. Process according to claim 1, wherein the reaction mixture further contains a catalytic amount of an additional acid compound.

6. The process according to claim 1 wherein the reaction is effected at a temperature between about 130° and 250° C.

7. Process according to claim 1, wherein the reaction is effected at a temperature of about 170° to 230° C.

8. Process according to claim 1, wherein the reaction conditions are maintained until about 20 to 90% of the acrylic compound has been converted.

9. Process according to claim 1, wherein the reaction is effected with acetone or cyclohexanone as the said ketone.

10. Process according to claim 1, wherein said acrylic compound is the nitrile, the methyl ester or the ethyl ester of acrylic acid, methacrylic acid or crotonic acid.

11. Process according to claim 1, wherein said cyclic secondary amine carries at least one substituent lower alkyl group of from 1 to 4 carbon atoms at one or more of the ring carbon atoms.

12. Process according to claim 1, wherein said cyclic secondary amine is selected from the group consisting of pyrrolidine, piperidine, morpholine and piperazine.

13. Process according to claim 1, wherein:
(a) said delta-keto-compound is delta-oxocaproic acid methyl ester;
(b) said ketone is acetone;
(c) said acrylic compound is methyl acrylate;
(d) said cyclic secondary amine is pyrrolidine;
(e) said acrylic compound of the adduct is methyl acrylate; and
(f) said adduct is methyl-$\beta$-pyrrolidin-1-yl-propionate, and wherein the reaction mixture further contains a catalytic amount of benzoic acid.

14. Process according to claim 5 wherein said additional acid compound is selected from the group consisting of acetic acid, adipic acid, benzoic acid, phenol, caproic acid, hydrochloric acid, phosphoric acid, sulfuric acid and ammonium chloride.

* * * * *